US012226071B2

(12) United States Patent
Kuhn et al.

(10) Patent No.: US 12,226,071 B2
(45) Date of Patent: Feb. 18, 2025

(54) IMAGE TRANSFER ARRANGEMENT AND METHOD FOR IMAGE TRANSFER

(71) Applicant: Schölly Fiberoptic GmbH, Denzlingen (DE)

(72) Inventors: Matthias Kuhn, Freiburg (DE); Alexander Kohler, Freiburg (DE); Stefan Schroer, Freiburg (DE)

(73) Assignee: Scholly Fiberoptic GmbH, Denzlingen (DE)

( * ) Notice: Subject to any disclaimer, the term of this patent is extended or adjusted under 35 U.S.C. 154(b) by 584 days.

(21) Appl. No.: 16/210,363

(22) Filed: Dec. 5, 2018

(65) Prior Publication Data

US 2019/0191963 A1    Jun. 27, 2019

(30) Foreign Application Priority Data

Dec. 21, 2017 (DE) .......................... 102017130980.2

(51) Int. Cl.
*A61B 1/00* (2006.01)
*H04N 23/60* (2023.01)

(52) U.S. Cl.
CPC ...... *A61B 1/00009* (2013.01); *A61B 1/00016* (2013.01); *A61B 1/00045* (2013.01); *H04N 23/60* (2023.01)

(58) Field of Classification Search
CPC ............ A61B 1/00009; A61B 1/00016; A61B 1/00045; H04N 5/232; H04N 2005/2255
USPC ........................................................ 370/905
See application file for complete search history.

(56) References Cited

U.S. PATENT DOCUMENTS

| | | | |
|---|---|---|---|
| 6,385,177 B1* | 5/2002 | Suda .................. | H04N 1/32702 370/310 |
| 6,878,106 B1 | 4/2005 | Herrmann | |
| 7,706,751 B2* | 4/2010 | Hakobyan ................. | H04J 3/26 455/63.1 |
| 8,266,333 B1* | 9/2012 | Wade .................... | H04N 19/436 710/36 |
| 8,905,918 B2 | 12/2014 | Kato | |
| 9,030,544 B2* | 5/2015 | Tashiro .............. | A61B 1/00059 348/74 |
| 2004/0073321 A1* | 4/2004 | Kondo ................. | H04N 7/0125 700/28 |
| 2004/0202200 A1* | 10/2004 | Hakobyan ................. | H04J 3/26 370/491 |
| 2005/0117121 A1* | 6/2005 | Meerleer ............ | H04N 21/4122 353/30 |
| 2006/0095093 A1* | 5/2006 | Bettesh .................. | A61B 5/073 607/60 |

(Continued)

FOREIGN PATENT DOCUMENTS

| | | |
|---|---|---|
| CN | 1473545 | 11/2004 |
| CN | 1827030 | 9/2006 |

(Continued)

*Primary Examiner* — Anh Tuan T Nguyen
*Assistant Examiner* — Shankar Raj Ghimire
(74) *Attorney, Agent, or Firm* — Volpe Koenig (57) ABSTRACT

An image transfer arrangement (1) for the wireless transfer of image information items between a transmitter (4) and a receiver (8), wherein at least two communication channels (11) which are physically independent of one another are formed between the transmitter (4) and the receiver (8) and enable impairment and interference-free communication.

17 Claims, 7 Drawing Sheets

(56) References Cited

U.S. PATENT DOCUMENTS

| | | | |
|---|---|---|---|
| 2006/0195602 A1* | 8/2006 | Shibata | H04N 21/23 348/E5.008 |
| 2006/0262186 A1* | 11/2006 | Avni | A61B 1/041 348/65 |
| 2007/0098379 A1* | 5/2007 | Wang | H04N 19/172 396/14 |
| 2007/0195923 A1* | 8/2007 | Netsch | G06T 11/005 378/4 |
| 2008/0100805 A1* | 5/2008 | Majumder | G06F 3/1446 353/30 |
| 2008/0100928 A1* | 5/2008 | Wilson | G02B 13/06 359/725 |
| 2008/0103363 A1* | 5/2008 | Levy | A61B 1/041 600/160 |
| 2008/0117968 A1 | 5/2008 | Wang | |
| 2008/0139881 A1* | 6/2008 | Cover | H04N 7/185 600/103 |
| 2009/0051762 A1* | 2/2009 | Shigemori | A61B 1/041 348/65 |
| 2011/0090056 A1 | 4/2011 | Kawasaki et al. | |
| 2011/0257481 A1 | 10/2011 | Ogawa et al. | |
| 2012/0154591 A1* | 6/2012 | Baur | B60R 1/08 348/148 |
| 2012/0274743 A1 | 11/2012 | Takasugi et al. | |
| 2012/0323073 A1* | 12/2012 | Azuma | A61B 1/05 600/110 |
| 2013/0124609 A1* | 5/2013 | Martinez | H04L 12/1877 709/203 |
| 2013/0265402 A1* | 10/2013 | Tashiro | A61B 1/00016 348/74 |
| 2013/0324794 A1* | 12/2013 | Cover | H04N 19/60 600/103 |
| 2013/0329028 A1* | 12/2013 | Saito | H04N 7/18 348/68 |
| 2014/0093238 A1* | 4/2014 | Roberts | H04B 10/116 398/43 |
| 2014/0163316 A1 | 6/2014 | Koide | |
| 2015/0190051 A1* | 7/2015 | Rajan | G06T 7/246 348/78 |
| 2015/0250387 A1* | 9/2015 | Hauger | G16H 30/20 600/424 |
| 2016/0174809 A1* | 6/2016 | Wang | A61B 1/00009 600/109 |
| 2017/0035272 A1 | 2/2017 | Endo | |
| 2017/0215713 A1* | 8/2017 | Takahashi | A61B 1/045 |
| 2017/0231008 A1* | 8/2017 | Ahn | H04W 74/006 |
| 2017/0353731 A1* | 12/2017 | Wade | H04N 7/181 |
| 2024/0349983 A1* | 10/2024 | She | H04N 23/555 |

FOREIGN PATENT DOCUMENTS

| | | | | |
|---|---|---|---|---|
| CN | 102224732 A * | 10/2011 | | A61B 17/00 |
| CN | 102440753 | 5/2012 | | |
| CN | 103458760 | 12/2013 | | |
| CN | 105377114 | 3/2016 | | |
| EP | 1719446 | 11/2006 | | |
| EP | 1974665 | 10/2008 | | |
| KR | 10925008 | 11/2009 | | |
| TW | 200627311 | 8/2006 | | |
| WO | 2006045011 | 4/2006 | | |
| WO | 2012065758 | 5/2012 | | |
| WO | WO-2012065758 A1 * | 5/2012 | | H04L 63/18 |
| WO | 2015050553 | 4/2015 | | |
| WO | WO-2016021994 A1 * | 2/2016 | | H04W 84/12 |
| WO | 0048506 | 8/2020 | | |

* cited by examiner

IMAGE TRANSFER ARRANGEMENT AND METHOD FOR IMAGE TRANSFER

INCORPORATION BY REFERENCE

The following documents are incorporated herein by reference as if fully set forth: German Patent Application No. 10 2017 130 980.2, filed Dec. 21, 2017.

BACKGROUND

The invention relates to an image transfer arrangement for the wireless transfer of image information items comprising a transmitter and a receiver.

Such transfer arrangements are known in principle and are used in endoscopy, in particular, in order to transfer the image data recorded by a camera head to an image display device. The advantage of such wireless image transfer arrangements is that the individual apparatuses are able to be set up more freely in space and no cables interfere with the actual work, for example, an operation.

Arrangements for wireless image transfer are known in principle, wherein the greatest problem here is the bandwidth and the security of the transfer. In practice, therefore, it is difficult to obtain a delay-free and interference-free image transfer. Particularly in endoscopy applications in which live images are transferred for an operation, an image transfer having delays or image drop-outs constitutes a major problem.

SUMMARY

It is an object of the invention, therefore, to provide an image transfer arrangement of the type mentioned above which enables a secure and delay-free image transfer at any time.

This object is achieved a method and an arrangement according to the invention. Preferred embodiments are described below and in the claims.

In the case of the image transfer arrangement according to the invention, provision is thus made, in particular, for at least two wireless communication channels that are physically independent of one another to be formed between the transmitter and the receiver. The two independent communication channels increase the security and reliability of the image transfer. In this regard, by way of example, both communication channels can be used for parallel image transfer, such that a redundancy is achievable. Delays in one communication channel can be compensated for by the second communication channel. Since the two communication channels are physically independent of one another, the probability of simultaneous interference or impairment of the two communication channels is reduced.

The invention affords the advantage that the at least two communication channels are operable and/or are operated asynchronously or with a temporal offset with respect to one another. Consequently, time losses in the transfer which arise as a result of a packetization into data packets are avoidable, for example by data being transferred on one communication channel, while data are prepared for transfer on the other communication channel, in particular by packetization.

If a plurality of data connections are set up on one physical communication channel, there is additionally the risk of the connections mutually interfering with one another. The physical separation of the communication channels can for example also be characterized by the fact that the image information items are transferable via the communication channels in a collision-free manner. What is thus achievable is that the communication channels do not mutually interfere with one another. Delays in the communication are thus reducible or even avoidable.

The physical separation of the communication channels can alternatively or additionally be characterized for example by the fact that a direct communication of the image information items is possible via each communication channel. In this case, by way of example, a direct connection is set up between the transmitter and the receiver, without a mediator station being interposed. Any delay is reducible further by the direct communication.

One particular advantage of a division of image data over a plurality of communication channels is that the image data can be transferred practically redundantly.

The communication channels are physically independent of one another. Each communication channel is configured for wireless data transfer and can be based for example on one of the following technologies. WLAN (WiFi), Bluetooth, NFC, ZigBee, analog radio, digital radio, light-based data transfer technologies, Wireless HDMI, optical directional radio (FSO), WiMAX, Infrared-based transfer technologies of the IrDA (IrPHY, IrLAP, IrLMP, IrCOMM, IrOBEX, IrSimple, IrSimpleShot, IrMC), general optical wireless transfer technologies, ISM band, LiFi (Light Fidelity), quantum communication, mobile radio network (CDMA, LTE, GSM inter alia), Wireless DVI.

The advantage of the invention consists, then, in the fact that two or more of the technologies are used in parallel and independently of one another. In this regard, it is possible, for example, to operate two communication channels on different WiFi bands (e.g. 2.4 GHz and 5 GHz). Alternatively, one communication channel uses WiFi and another uses an optical data transfer. Overall there are very many combination possibilities here, such that specific technologies may be advantageous in each case for different applications. Therefore, the invention in principle is not intended to be restricted to the abovementioned examples or specific combinations or technologies.

Furthermore, it may be expedient if, in order to achieve ever shorter delays between image recording and display, which is highly advantageous or even necessary in particular for surgical interventions, but also for other examinations, the number of physical communication channels realized is greater than two. As a result, the bandwidth increases in principle with each additional communication channel.

In one advantageous embodiment, an image recording device, which has in particular an image sensor, can be connected or connectable to the transmitter. Such an image recording device can be for example a video head of an endoscope, a microscope, an ultrasound head or any other image source. The image recording device can be connectable to the transmitter for example via a wired interface. In this way, the transmitter according to the invention can be connected to different image sources, in particular image sensors. In this way, existing image sensors can be retrofitted or combined with a wireless image transfer.

In an alternative embodiment, the image recording device is permanently connected to the transmitter, for example within a common housing.

In a further embodiment of the invention, it may be advantageous if the transmitter has a preferably additional image output device, in particular image display device, for example a display having reduced image resolution. The advantage here may be that image monitoring is already possible on the transmitter, such that an image recording device can be corrected in terms of position or an image excerpt can be altered, without looking at an external screen. The handling of an image recording device can be significantly simplified as a result. The or a further, additional image display device can also be arranged at the image recording device.

In one advantageous embodiment of the invention, an image display device can be connected or connectable to the receiver. The image display device is preferably a monitor in order to represent the highest possible image resolution.

In a further advantageous embodiment, an image processing device, for instance a computer, can be connected or connectable to the receiver, for example for an automated desired image comparison. The image processing device can optionally have a screen in order to monitor the image transfer, for example.

The image recording device can also have more than one image sensor, in particular for recording a 3D image or for recording images in different spectral ranges. In this case, the different physical communication channels can also be used separately for the two or more than two image sensors present. In this way, the image information of each image sensor can be transferred independently via a respective communication channel.

An alternative embodiment of the invention provides for a plurality of transmitters to be present, which are connected to a receiver via the communication channels. This is advantageous in particular if a plurality of image sensors are used in order for example to record an object from a plurality of positions and/or in a plurality of spectral ranges simultaneously.

Provision can also be made for different color values of the recorded image to be transferred via the separate physical communication channels.

In the case of the image division, it may be advantageous if the physical communication channels are fed alternately with individual images, so-called frames, or with a pixel pattern of the individual frames, which extend in each case over the entire image extent. Only a partial image is thus transferred on each communication channel. The susceptibility to interference is reduced as a result. If one communication channel fails or is subjected to interference, a total image can also be combinable from the rest of the communication channels.

In this case, the image division can be carried out in various ways. In this regard, by way of example, a full image could respectively be transferred on a first communication channel, and the subsequent full image then on the next communication channel. However, the communication channel could also be changed for each image line or on the basis of a pixel pattern or, as already described above, the color or image information items of an image sensor on each communication channel.

This makes it possible, in particular in surgical applications, for the surgeon still to obtain a full image, even if an image communication channel fails.

Provision can be made for a plurality of displays to be provided at the receiver end. This is advantageous in particular in the case of complicated surgical interventions, since the various persons involved can each have their own display.

In this case, provision can be made for the displays to be driven by a common receiver or to be supplied by separate receivers. Said separate receivers can jointly utilize in each case the physical communication channel provided, or provision can be made for each receiver to set up separate physical communication channels with the transmitter.

To put it another way, the transmitter can be designed for 1:n operation. The transmitter and the receivers then have in each case at least the same number of communication channels. The receivers combine in each case on the same communication channels. Since only reception by a plurality of apparatuses takes place, mutual impairment of the signal quality of the receivers is avoidable.

On the other hand, the transmitter and the receiver can also be designed for 1:1 operation. Here the transmitter, for M receivers with N communication channels in each case, must have M×N communication channels. It may be advantageous here, however, for each individual communication channel to be a direct connection between exactly one transmitter channel and one receiver channel. That means that if a communication channel is subjected to interference, only exactly one image display device is affected thereby and the full image data still arrive on the other communication channels.

Provision can also be made for the further display in turn to be wirelessly connected to the first receiver.

One advantageous embodiment provides for a communication channel to be configured for transmitting control commands and/or measurement data. This can be implemented in particular by way of a bidirectional communication channel. Expediently, at least one communication channel is configured as an image channel, preferably unidirectionally from the transmitter to the receiver.

Generally, the terms transmitter and receiver are in relation to the image transfer direction, that is to say the main image data stream. The transmitter is thus always at the image generation end, independently of whether communication channels that transmit in the other direction are also present.

In one expedient embodiment, the first communication channel can be oriented unidirectionally from the transmitter to the receiver in order to transfer image data. The second communication channel is in turn also oriented unidirectionally, but from the receiver to the transmitter, in order to transfer control commands, for example.

Here provision can also be made, for example, for acknowledgements of control commands to be sent back in transfer gaps of the image channel or in a manner encoded in the image data. Consequently, a control group is able to be formed between the transmitter and the receiver only with unidirectional communication channels.

Generally, the unidirectional channels can be oriented arbitrarily between transmitter and receiver.

In a further advantageous embodiment, at least one of the communication channels can be configured as bidirectional. For this purpose, the transmitter itself can contain a receiving component and the receiver itself can contain a transmitting component in order to transmit bidirectional data via the individual communication channels. It is also possible for only individual communication channels to be configured as bidirectional. In this way, data can be transferred in both directions.

In this way, any delay can be minimized by virtue of the second channel, for example, being used for communicating measurement and/or control data.

Provision can also be made for control commands which arise for example as a result of image processing at the receiver end to be transferred back independently of the image data stream.

Moreover, provision can be made for measurement data to be transferred via the or a further communication channel. In this regard, by way of example, an endoscope head can have a temperature sensor or further sensors, the measurement values of which can be transferred independently of the image data.

In one advantageous embodiment of the invention, three communication channels are formed between the transmitter and the receiver. This can be used for example for transferring image data via the first communication channel, measurement data via the second communication channel and control commands via the third communication channel. In this case, the first and second communication channels can be oriented unidirectionally from the transmitter to the receiver, and the third communication channel in the other direction. However, it is also possible for at least one of the communication channels to be configured as bidirectional.

Another expedient application provides for image data to be communicated via a first communication channel from the transmitter to the receiver and reduced image data to be communicated via a second communication channel and control commands to be communicated via a third communication channel back from the receiver end to the transmitting end. As a result, it is possible to carry out image monitoring with reduced image data at the transmitter end, wherein the computing capacity for this need not be arranged in the transmitter, as a result of which structural space and costs can be saved.

Furthermore, it may be advantageous if at least two of the communication channels are configured for asynchronous data transfer.

This has the advantage, in particular for example in the case of the use as two image transfer channels, that information items can be packetized independently of one another, with the result that dead times which are otherwise present and which occur during the packetization of image data can be covered or utilized by the other communication channel.

In one advantageous embodiment of the invention, the transmitter and/or the receiver for each physical communication channel in each case have/has an individual interface component and/or an individual address. In this way, a physical separation of the individual channels is able to be realized in a simple manner. In this case, the address can be a MAC or IPv6 address, for example, with which an unambiguous assignment is possible. As a result, the communication channels are feedable with data in a targeted manner, as a result of which for example image data and measurement data are addressable to different receivers.

It may be particularly advantageous if the communication channels are configured as radio link and/or optical connection, for example via radio or via infrared or suchlike near-field communication and/or Wifi or other transfer techniques.

In one advantageous embodiment, a preprocessing configured for delay-free image processing can be disposed upstream of the transmitter.

This can be for example a brightness regulation or other steps for adaptation to the measurement conditions of the individual measurement pixels.

Said preprocessing can also be drivable via a separate bidirectional communication channel.

However, it is also conceivable for all these processing steps to be carried out only at the receiver end or in part at the transmitter end and the receiver end.

In one embodiment of the invention, it may be advantageous if the transmitter has a data and/or signal distributor. It is thus possible, in particular, to distribute data from a data source between a plurality of communication channels. As a result, by way of example, the transfer bandwidth can be increased and/or data redundancy can be obtained.

This distribution can be carried out for example image by image or line by line or else into individual color channels.

The transmitter can alternatively or additionally also have a multiplexer, which feeds the at least two communication channels with data and/or signals. In this way, it is possible, for example, to allocate data from a plurality of signal sources, such as measurement signals, for instance, to the communication channels present.

It is advantageous, in particular, if the transmitter has an image division for distributing the image information items between the communication channels present.

In the case of the image division, it is advantageous if the two (or more) physical communication channels are fed alternately with individual images, so-called frames, or with a pixel pattern of the individual frames, which extend in each case over the entire image extent.

This makes it possible for a full image still to be receivable, even if an image communication channel fails or is subjected to interference.

Provision can also be made for different color values of the recorded image to be transferred via the separate physical communication channels.

In one embodiment, it may be advantageous if a marking device is disposed upstream of the transmitter, which marking device adds to the image information items communicated via the at least two communication channels a respective identification information item, which serves for combining the transferred image information items at the receiver end.

Preferably, the identification information is encoded in payload data, in particular the image data and/or outside a header and/or footer of a protocol. It is advantageous in this case that the reconstruction is possible independently of a protocol used and thus in particular in a cross-channel manner.

This can be achievable for example by allocating image pixels in the edge region of the image to be transferred, for example outside a field of view predefined by an optical system, or by other grey-scale or color encodings or in some other way, for example in the blanking interval.

In this case, a sorting algorithm or an encoding can be used, which enable combination at the receiver end even if the order of the arriving individual images is interchanged because the individual physical communication channels had transfer times of different lengths.

In one development, provision can be made for a memory for storing the image information items to be present, preferably in the transmitter, in particular between the image sensor and the transmitter.

This has an advantage in particular if the display or the receiving end is configured as a monitor without relatively high computing power.

In this case, provision could be made of a device which triggers a wireless data communication, for example via one or more of the communication channels present, if the memory is intended to be read. This can be triggered for example by the beginning of a charging process.

For recycling the image recording device after use, it may be advantageous if the transmitter end, in particular the image sensor and the transmitter, are arranged in an encapsulated or hermetically sealed housing.

The transmitter end can be configured as a camera head and/or as an endoscope or some other optical instrument or some other optical system, for example an exoscope, which is arranged outside the patient's body for certain open operations, or a microscope.

An image sensor according to the invention is generally a sensor that provides a spatially resolved measurement result. Said measurement result can be obtained by an optical image recording or in some other way, for example by an ultrasonic measurement.

Besides the image transfer arrangement, the invention also encompasses an image recording device comprising an image sensor and comprising a transmitter with at least two communication channels. In this case, the image sensor and the transmitter can be integrated in one housing or be arranged in separate apparatuses. The number of image sensors and communication channels can be chosen as desired.

In particular, the image recording device is suitable for use in an image transfer arrangement according to the invention.

The image recording device can also have more than one image sensor, in particular for recording a 3D image or for recording images in different spectral ranges. In this case, the different physical communication channels can also be used separately for the two or more than two image sensors present.

Furthermore, the invention also encompasses an image display device comprising a screen and comprising a receiver with at least two communication channels, in particular for use in an image transfer arrangement according to the invention.

The apparatuses at the receiver end can integrate the receiver and the display, for example in the form of a tablet, smartphone or the like.

It is also possible for the display to be configured as a television or monitor equipped with intelligence, or else as a purely directly drivable monitor. Furthermore, it is also possible for the receiver and the screen to be arranged in separate apparatuses. In this way, it is easily possible to connect a plurality of screens to a receiver.

In particular, the invention encompasses an endoscope arrangement comprising an image recording device described above. In this case, the at least one image sensor and the transmitter can be integrated in a camera head. However, it is also possible for the image sensor to be arranged in a changeable camera head and for the transmitter to be arranged in an endoscope handle.

The invention furthermore encompasses an endoscope arrangement comprising an endoscope and at least one image display device.

Besides the image transfer arrangement, the invention also encompasses a method for transferring image information items between a transmitter and a receiver, in particular an image transfer arrangement according to the invention, wherein at least two physically independent communication channels are used and wherein the image information items are divided between the communication channels.

The division of the image information items between a plurality of communication channels makes it possible to obtain redundancy, for example. In the case of the image division, it may also be advantageous if the two physical communication channels are fed alternately with individual images, so-called frames, or with a pixel pattern of the individual frames, which extend in each case over the entire image extent.

It may be advantageous in particular if a total image is divided between the at least two communication channels.

In the case of the division of an image between a plurality of communication channels, it may be advantageous if there is encoded in the image information items transferred per communication channel in each case an identification information item, which allow a reconstruction of the original image information items at the receiver end. A cross-channel reconstruction of an image information item is thus made possible. The identification information item is preferably an order information item. Consequently, a temporal sequence is easily reconstructable in a cross-channel manner.

Preferably, the identification information is encoded in payload data, in particular the image data and/or outside a header and/or footer.

Particularly when the identification information is accommodated in the payload data, it is possible to dispense with the transfer of metadata, as a result of which the transfer rate is able to be increased further.

Consequently, an order present at the transmitter end is reconstructable in a cross-channel manner at the receiver end. This also facilitates the handling of the image information items if interference with the data transfer is present in a communication channel.

In one embodiment of the method according to the invention, it is therefore provided that if an image is missing in the reconstructed order, the associated images that produce a total image are omitted altogether, in particular wherein the previously combined image is presented instead. In this way, a complete total image is always displayable, even if for example individual partial images of a communication channel subjected to interference cannot be received. For the surgeon it is generally more expedient for a transferred image to be repeated briefly, instead of the image being disturbed by flicker.

Besides the division of the image data, it may also be advantageous if one of the at least two communication channels is used for transferring control commands and/or measurement data. In this way, mutual interference between the image data and the control data does not arise and the full transfer bandwidth is always available.

BRIEF DESCRIPTION OF THE DRAWINGS

The invention is described in greater detail below on the basis of some exemplary embodiments with reference to the accompanying drawings.

In the figures.

DETAILED DESCRIPTION

Figure 1:
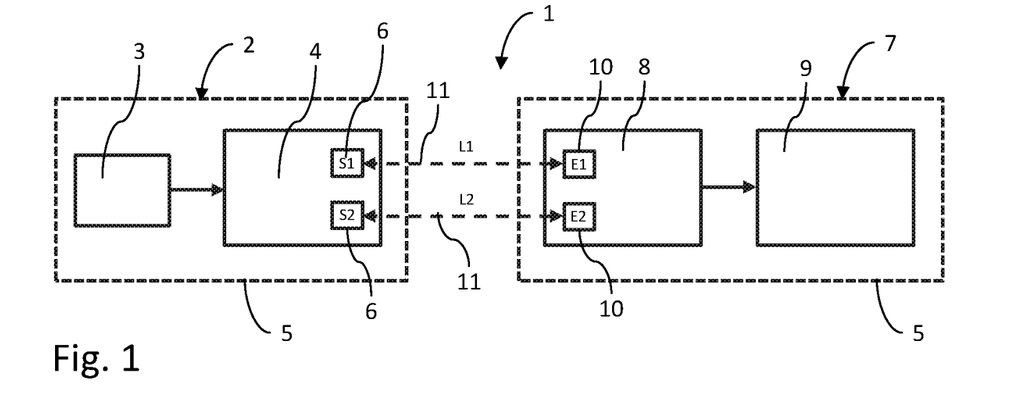
FIG. 1: shows an image transfer arrangement with two communication channels with a transmitter with an integrated image recording device and a receiver with an integrated image display device.

FIG. 1 shows a schematic block illustration of an image transfer arrangement 1 according to the invention. An image recording device 2 has an image sensor 3 and a transmitter 4, which are integrated in a common housing 5 in one apparatus.

The transmitter 4 has two mutually independent transmitting components 6 as interface components.

An image display device 7 has a receiver 8 and a screen 9, which is integrated with the receiver 8 in a housing 5 of an apparatus.

The receiver 8 has two receiving components 10 as interface components, which in conjunction with the transmitting components 6 of the transmitter 4 form two physically separate communication channels 11.

The communication channels 11 can be configured for example as optical transfer link or as radio interface. This can vary depending on the field of application, and even mixed forms are possible.

In one advantageous example, the communication channels are configured as WiFi connection, wherein one communication channel 11 is in the 2.4 GHz band and the second communication channel 11 is in the 5 GHz band. In this way, the two communication channels are sufficiently physically separated, as a result of which mutual influencing and interference does not occur and a sufficient immunity to interference is provided.

In the case of a large number of communication channels, the latter could also be on different channels of a radio band.

In the case of optical connections, the two communication channels 11 could transmit for example at different wavelengths (infrared and blue) and/or with different polarization.

The image information items recorded by the image sensor 3 are divided between the two communication channels 11 in the transmitter 4 and are transferred to the receiver 8, preferably asynchronously and wirelessly. In the simplest case, the image information items are in each case transferred completely on both communication channels 11. A parallel and thus redundant data transfer thus takes place.

In the receiver 8, the image information items are combined again in the correct order and guided to the screen, where an image is represented.

Alternatively, by way of example, a division into fields can also be carried out, which fields are transferred alternately via a respective communication channel 11 and are joined together again to form a total frame at the receiver end. Such an interlacing image transfer is known from video and television technology, for example, wherein here there is the advantage that the two fields can be transferred simultaneously via the two communication channels 11 and, consequently, no delays take place.

In addition, further image divisions are also possible, as described further above.

Figure 2:
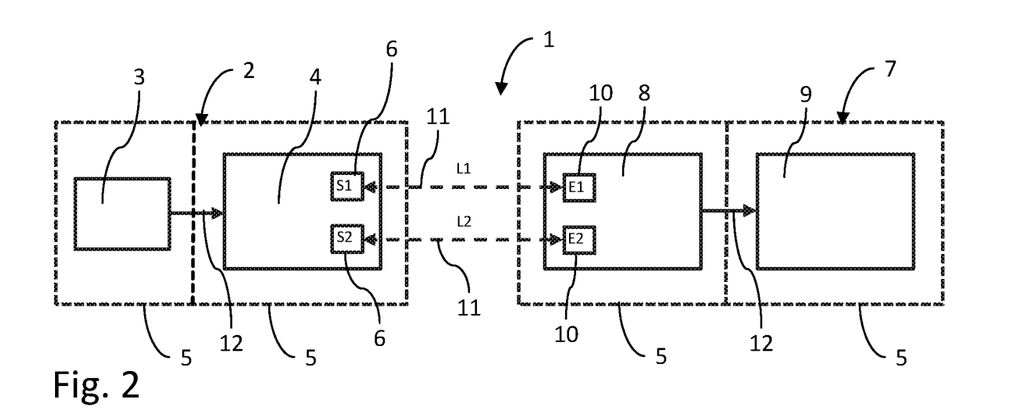
FIG. 2: shows an image transfer arrangement with two communication channels with a transmitter with a connected image recording device and a receiver with a connected image display device.

As indicated schematically in FIG. 2, the image sensor 3 can also be arranged in a separate apparatus, wherein the image sensor 3 and the transmitter 4 here are connected to one another by a wired interface 12. Such an image transfer arrangement 1 could be an endoscope, for example, in which the image sensor 3 is arranged in a changeable camera head and the transmitter 4 is arranged in an endoscope handle 17. In the example in FIG. 2, the screen 9 of the image display device 7 is also arranged in a separate apparatus from the receiver 8. The screen 9 can also be arranged in a further separate apparatus, for example a monitor 21 (FIG. 13), which is connectable to the receiver 8.

Instead of the image display device 7 or the screen 9 or in addition thereto, in every embodiment shown, including below, an image processing device can be connected to the receiver 4. Such an image processing device can be configured for example for automatic desired image comparison, wherein the recorded images are compared in each case with a desired image in order thus to identify for example erroneous or damaged parts or abnormal deviations in an automated manner.

Figure 3:
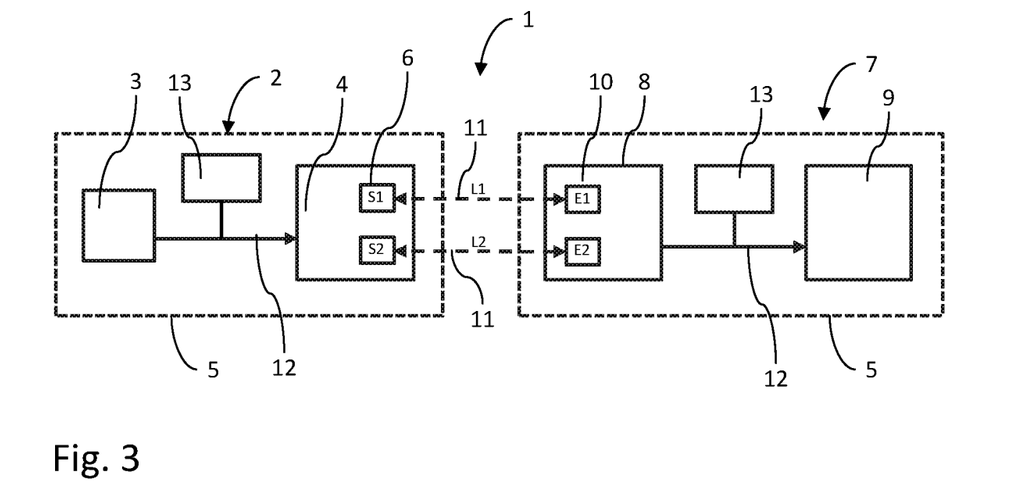
FIG. 3: shows an image transfer arrangement with two communication channels with a transmitter with an integrated image recording device and a memory and a receiver with an integrated image display device and a memory.

The image transfer arrangement 1 in FIG. 3 substantially corresponds to FIG. 1. However, the image recording device 2 has a memory 13 between the image sensor 3 and the transmitter 4, the image data stream of the image sensor 3 being able to be stored by said memory. A memory 13 can alternatively or additionally be arranged between the receiver 8 and the screen 9, as illustrated in FIG. 3.

It goes without saying that the image recording devices 2 and the image display devices 7 in FIGS. 1 to 3 are combinable with one another in any desired manner.

Figure 4:
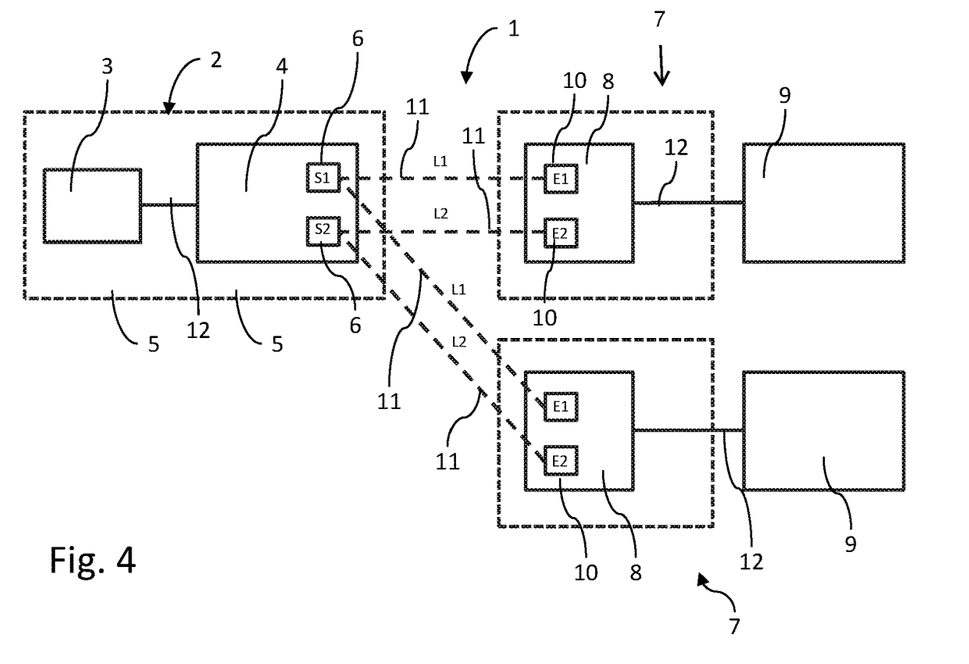
FIG. 4: shows an image transfer arrangement with two communication channels with a transmitter with an integrated image recording device and two receivers each with a connected image display device.

In the case of the image transfer arrangement 1 in FIG. 4, a second image display device 7 is then present, which is identical to the first image display device 7. In this case, the receiver 8 of the second image display device 7 combines with the same communication channels 11 in parallel with the first image display device 7. The two image display devices 7 thus receive the same image information items.

This is advantageous in particular if a plurality of persons are intended to see the same image content and each use their own image display device 7. In this case, these image display devices can also be arranged in different rooms.

Figure 5:
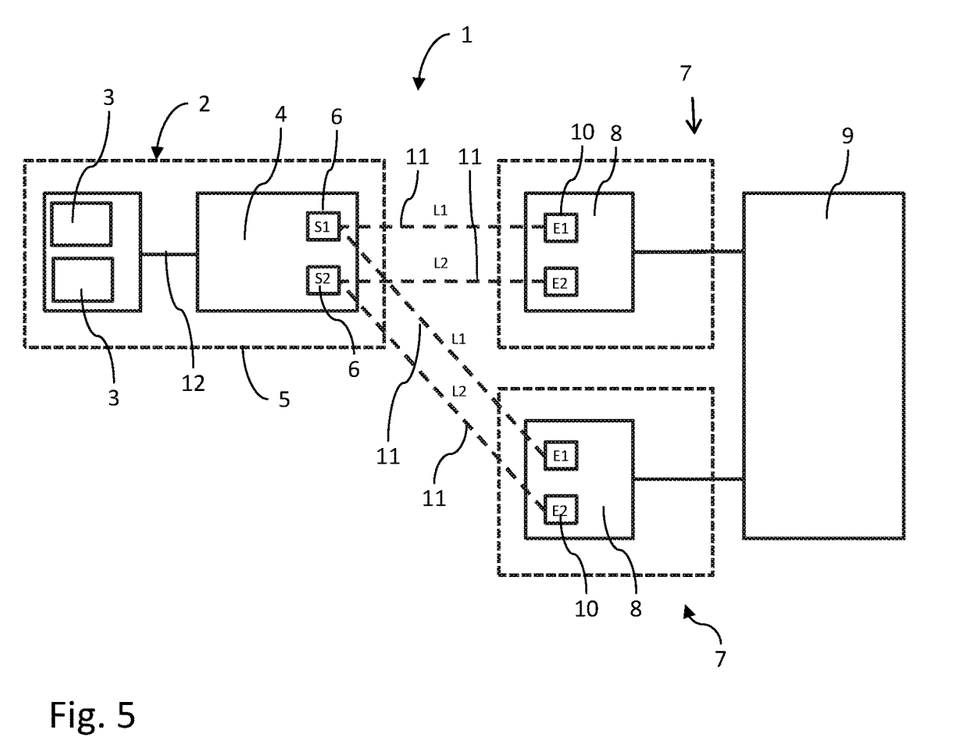
FIG. 5: shows an image transfer arrangement with two communication channels with a transmitter with an integrated image recording device with two image sensors and two receivers connected to an image display device.

In the case of the image transfer arrangement 1 in FIG. 5, the image recording device 2 has two image sensors 3, which for example serve for 3D recording or are sensitive in different spectral ranges, for example infrared and visible light.

It may be advantageous here if the image information items of an image sensor 3 are transferred via a respective one of the communication channels 11.

In this embodiment, two receivers 8 are present, which however are both connected to a common screen 9, in particular for 3D representation.

In the embodiments in FIGS. 4 and 5, the communication channels 11 are preferably oriented in each case unidirectionally from the transmitting end to the receiver end. This may be the case for example for transferring image data and measurement data.

In principle, however, in the case also of these embodiments with a plurality of receivers 8, a bidirectional data transfer is possible, for instance for control commands. In this case, however, it is expedient if an, in particular physical, collision detection and resolution takes place, such that the transmitter 4 does not receive and carry out contradictory control commands, for example. For this purpose, a prioritization of the data can also be set up, thereby stipulating which receiver 8 is given priority in the case of a collision. It could also be stipulated that control commands are accepted only from one receiver, in which case the commands of the other receivers would be ignored.

Figure 6:
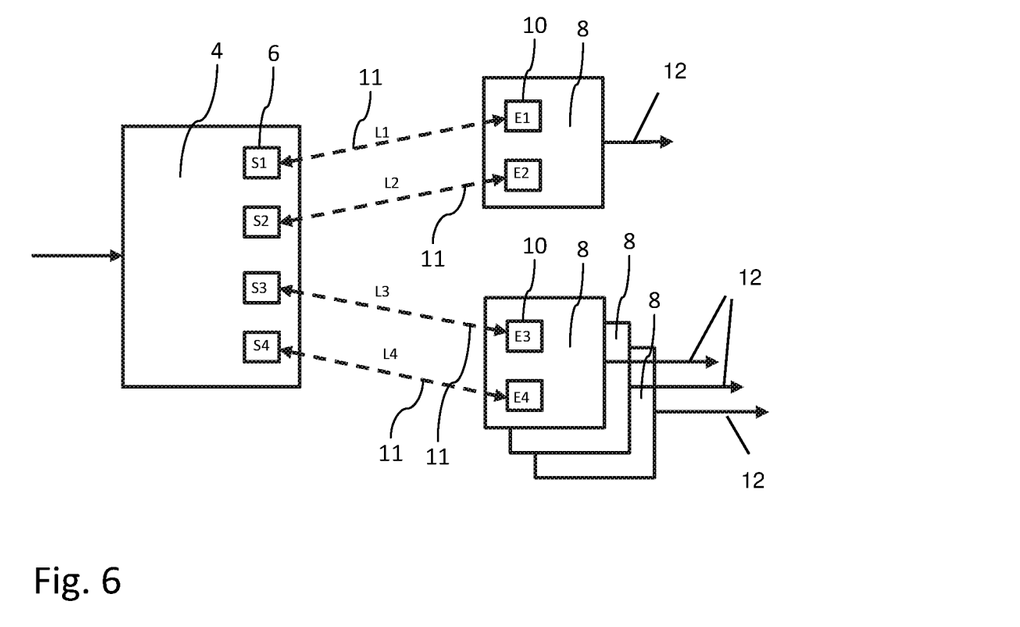
FIG. 6: shows an image transfer arrangement with a transmitter with four communication channels and a plurality of receivers.

FIG. 6 shows a transmitter 4 having four transmitting components 6. Two receivers 8 each having two receiving components 10 are arranged at the receiver end. Here, therefore, in each case two separate communication channels 11 are formed between the transmitter 4 and the receivers 8. Consequently, the receivers 8 could obtain different image information items or other data. In the example, alongside the lower receiver in the illustration, further parallel receivers 8 are shown, which can be connected in parallel analogously to FIG. 4. Additional wired interfaces 12 are shown for the receivers 8. It goes without saying that further receivers 8 can also be present in parallel with the upper receiver.

Figure 7:
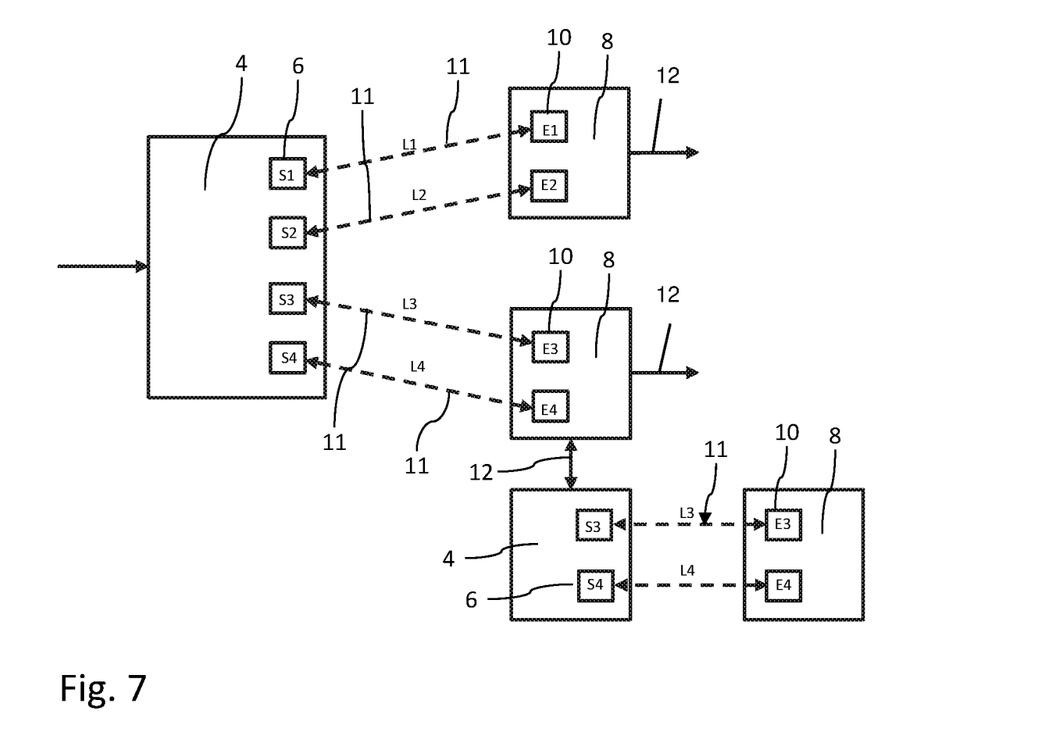
FIG. 7: shows an image transfer arrangement with a transmitter with four communication channels and a plurality of receivers and a cascaded image transfer arrangement.

In the case of the embodiment in FIG. 7, a further transmitter 4 is connected to the lower receiver 8 in the illustration, said further transmitter in turn driving a receiver 8. In this way, the range of the wireless connection can be increased if this is necessary. In this case, the receiver 8 is preferably connected to the further transmitter 4 via a wired interface 12. Additional wired interfaces 12 are shown for two of the receivers 8.

Figure 8:
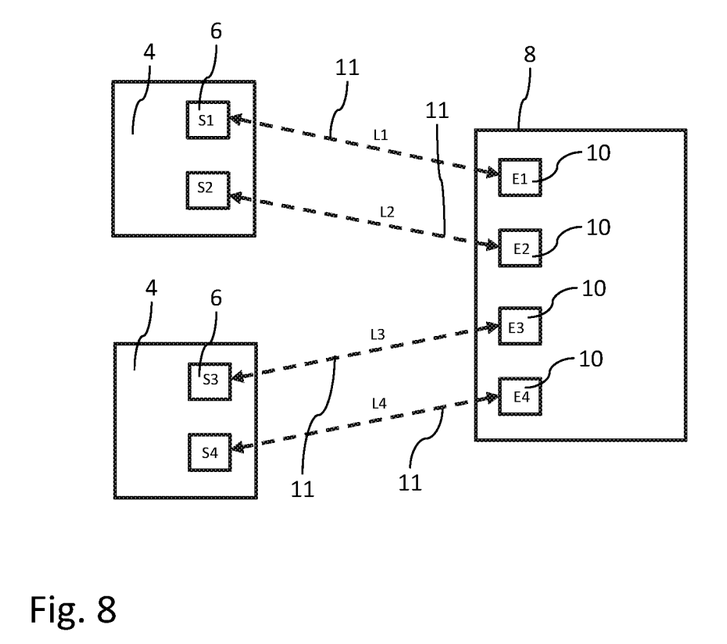
FIG. 8: shows an image transfer arrangement with two transmitters and a receiver with four communication channels.

FIG. 8 shows an alternative embodiment of the invention with two transmitters 4 each having two transmitting/receiving components 6. A receiver 8 having four independent transmitting/receiving components 10 is present at the receiver end. Each transmitter 4 can be connected for example to an image sensor 3 in accordance with FIG. 2 in order for instance to record a stereoscopic image or images in different spectral ranges. The receiver 8 is connectable to or equipped with one or more screens 9 and/or an image processing, for instance a computer.

Figure 9:
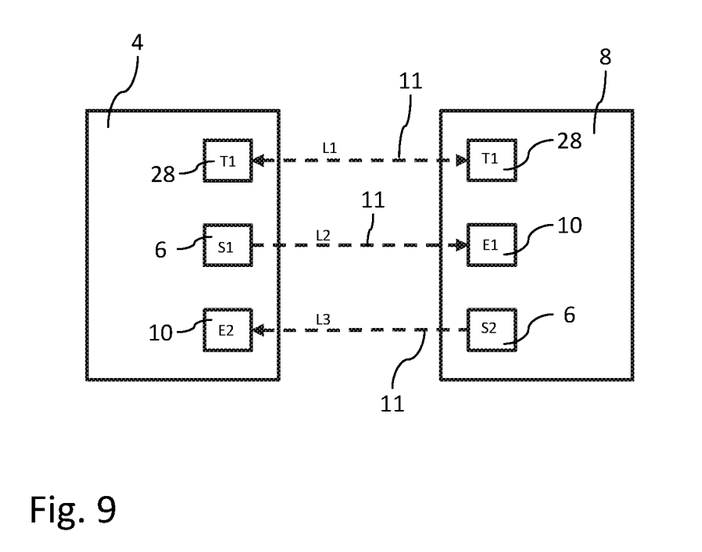
FIG. 9: shows an image transfer arrangement with one bidirectional communication channel and two unidirectional communication channels.

FIG. 9 shows a general image transfer device comprising three communication channels 11. In this example, the first communication channel L1 is configured as bidirectional for transferring control commands. For this purpose, the transmitter 4 and the receiver 8 respectively have a transmitting/receiving component 28. The second communication channel L2 is oriented unidirectionally from the transmitter 4 to the receiver 8 and is configured for image transfer, for example. The third communication channel L3 is oriented unidirectionally from the receiver 8 to the transmitter 4, wherein here for example an image data stream with reduced resolution can be transferred back.

Any desired combination is conceivable besides the orientation of the three communication channels 11 shown. In this regard, the second communication channel L2 could also be oriented for transferring measurement data from the transmitter 4 to the receiver 8. The communication channel L1 for the control commands can also be oriented unidirectionally from the receiver 8 to the transmitter 4. In this case, it would be possible to send back acknowledgements for the control commands with the image data or the measurement data via a different communication channel 11.

The physical separation of the communication channels 11 enables the targeted addressing and feeding with data. In this way, for instance, measurement data can be transmitted to a different receiver than image data.

Figure 10:
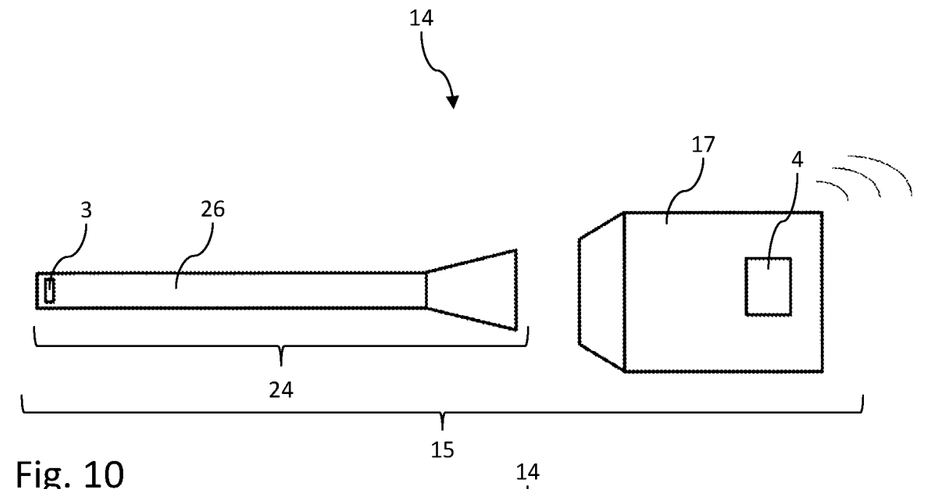
FIG. 10: shows an endoscope with a changeable probe with image sensor and a handle with transmitter.

FIG. 10 shows an endoscope 15, for example, which is configured as an endoscope arrangement 14 in accordance with FIG. 2. The endoscope 15 has a changeable probe 24, in which an image sensor 3 is arranged. The changeable probe 24 is connectable to an endoscope handle 17. The endoscope handle 17 has a transmitter 4 with at least two communication channels 11.

Figure 11:
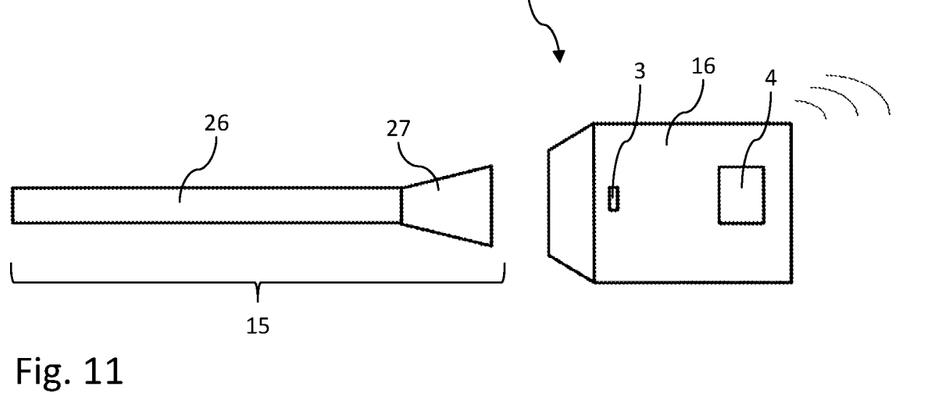
FIG. 11: shows an optical endoscope with a camera head with image sensor and transmitter.

FIG. 11 shows an alternative embodiment of an endoscope arrangement 14 in accordance with FIGS. 1 to 3. The endoscope arrangement 14 has a conventional endoscope 15, for example comprising rod lenses or a fiber-optic unit. The endoscope 15 has an endoscope shaft 26 and an eyepiece 27 arranged thereon. The endoscope 15 is connectable to a camera head 16. The camera head 16 has an image sensor 3 and a transmitter 4.

Figure 12:
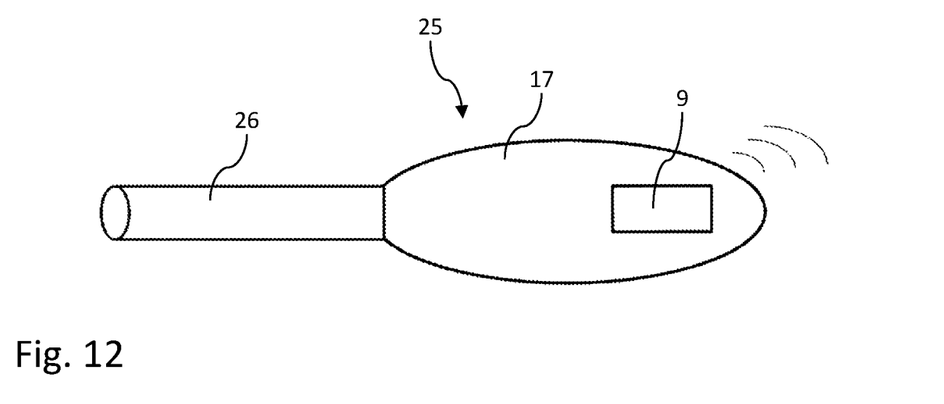
FIG. 12: shows an integral video endoscope with transmitter.

FIG. 12 shows a further embodiment of an endoscope arrangement 14 with an integral video endoscope 25. The video endoscope 25 has an integrated image sensor 3 and a transmitter 4 (neither of which is explicitly illustrated). Furthermore, the video endoscope 25 has a screen 9 having a reduced resolution, which can be used for position monitoring.

Figure 13:
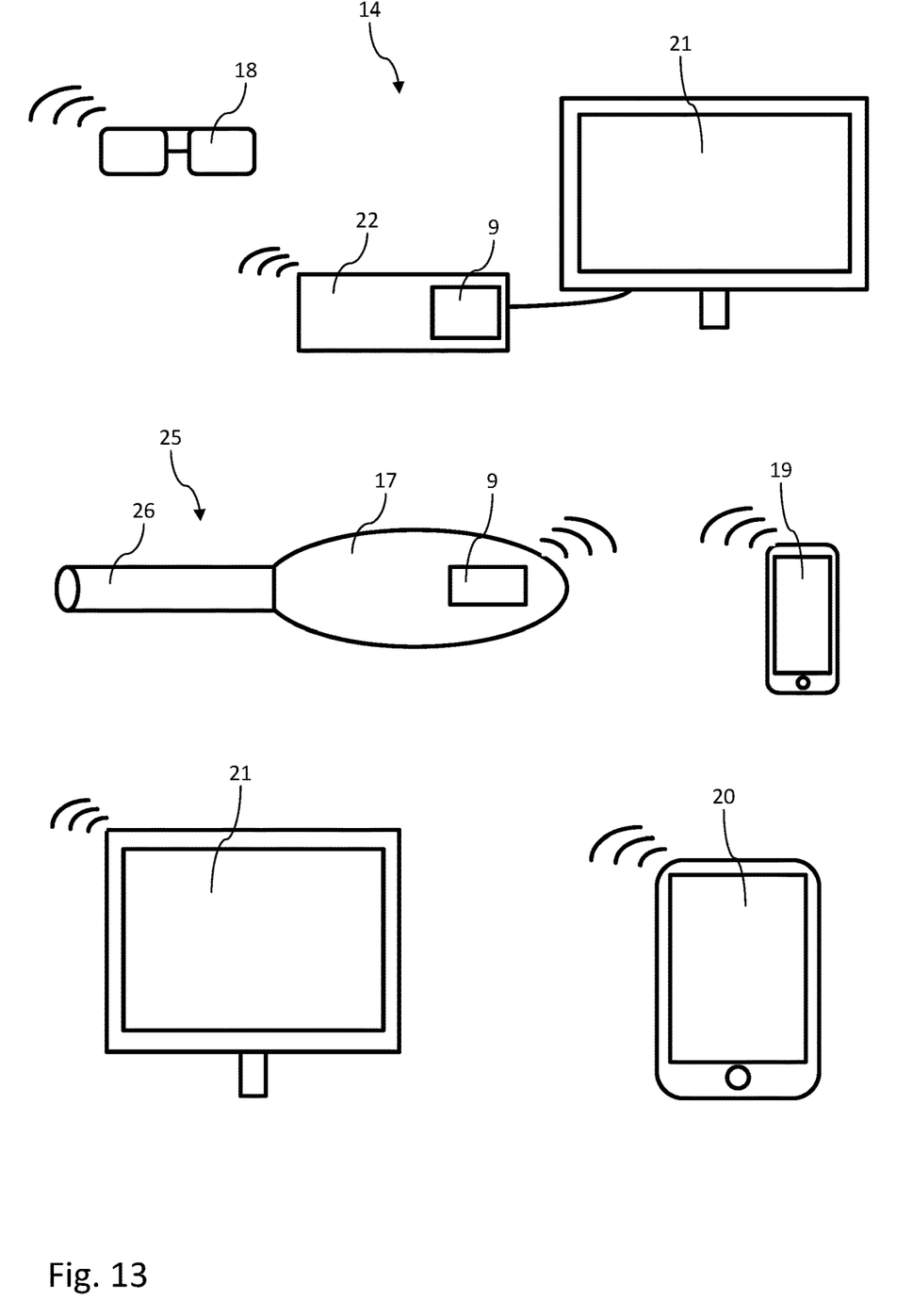
FIG. 13: shows an endoscope arrangement according to the invention with a plurality of receivers.

FIG. 13 shows by way of example an endoscope arrangement 14 with a video endoscope 25 with a plurality of additional image display devices 7.

By way of example, VR (virtual reality), MR (mixed reality) or AR (augmented reality) glasses 18, a monitor 21 with a separate camera control unit 22 with receiver 8 and a dedicated screen 9, a smartphone 19, a tablet computer 20 and a monitor 21 with integrated receiver can be seen here as image display devices 7. The image display device 7 can also be a projector.

Figure 14:
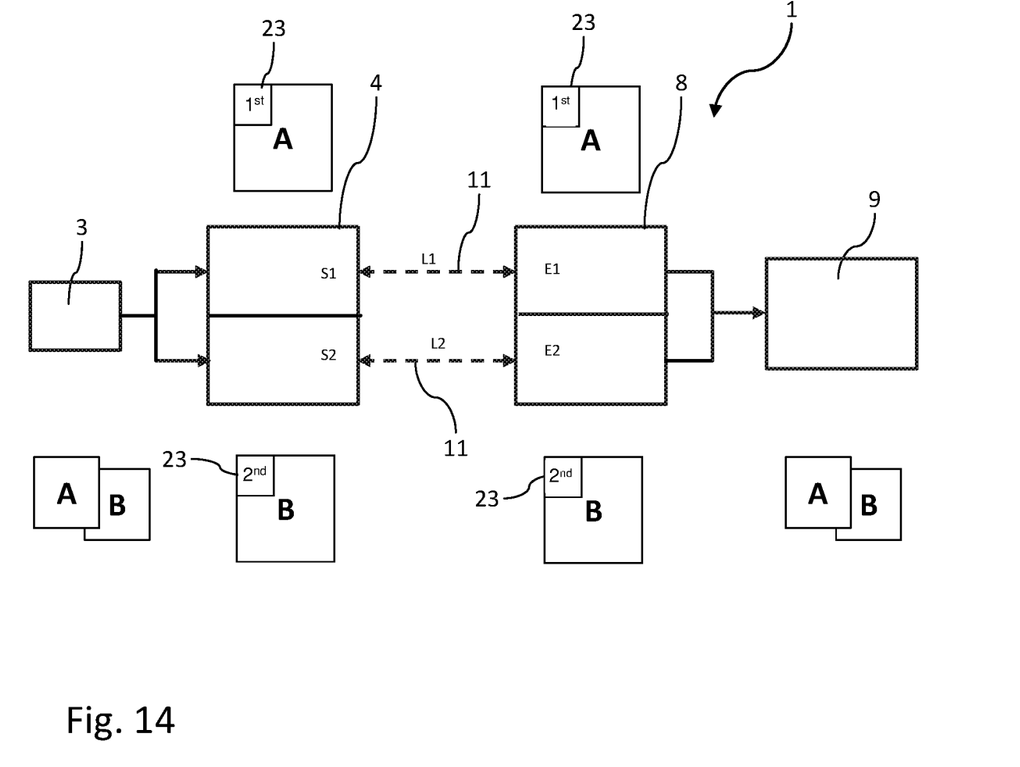
FIG. 14: shows a schematic illustration of the image division for the image transfer with an image transfer arrangement.

FIG. 14 shows an image transfer arrangement 1 which substantially corresponds to FIG. 2. In this example, successive images A and B are transmitted alternately via the two communication channels 11.

The at least two communication channels are operated asynchronously and/or with a temporal offset with respect to one another. Time losses in the transfer which arise as a result of a packetization into data packets are thus avoidable. For this purpose, data are transferred on one communication channel, while data are prepared for transfer on the other communication channel, in particular by packetization. The packetization adds to the payload data in particular headers and/or footers stipulated by a data protocol.

In the example shown, therefore, the image A is transmitted via the upper communication channel L1 and the image B is transmitted via the lower communication channel L2.

The individual successive images A and B of the image sensor 3 have to be marked prior to the distribution between the communication channels 11 in the transmitter 4 in order that they can be brought into the correct order again for representation by the receiver 8.

For this purpose, order information items 23 are stored in each individual image A and B. Possibilities for marking in the image are, for example:

continuous colored marking (image A→$1^{st}$ pixel top left green, image B→$2^{nd}$ pixel top left green)

utilizing the color information in the pixel to store a number: each pixel contains at least one item of information (grey-scale level, R value, G value, B value, IR value, . . . ); the value of the information is stored as a number. One example would be the grey-scale level, which can assume e.g. a value of 0-255. This value can be overwritten with a consecutive number reflecting the order of the images.

the order could also be concomitantly impressed as metainformation, such as e.g. the location in the case of a JPG.

generally there is always the possibility of adding information for the order to the image by way of an additional header.

The advantage of the invention consists, then, in the fact that the order information items 23 can be encoded within the actual image information. In this way, the transfer of further metadata could be dispensed with, with the result that the bandwidth for payload or image data is increased.

LIST OF REFERENCE SIGNS

1 Image transfer arrangement
2 Image recording device
3 Image sensor
4 Transmitter
5 Housing
6 Transmitting component
7 Image display device
8 Receiver
9 Screen
10 Receiving component
11 Communication channel
12 Wired interface
13 Memory
14 Endoscope arrangement
15 Endoscope
16 Camera head
17 Endoscope handle
18 VR glasses
19 Smartphone
20 Tablet computer
21 Monitor
22 Camera control unit
23 Order information
24 Changeable probe
25 Video endoscope
26 Endoscope shaft
27 Eyepiece
28 Transmitting/receiving component
S1 . . . 4 Transmitting component
E1 . . . 4 Receiving component
T1 Transmitting/receiving component
L1 . . . 4 Physical communication channel

The invention claimed is:

1. An endoscope system, comprising:
an image transfer arrangement (1) for the wireless transfer of image information items, the image transfer arrangement having a device (2) including at least one transmitter (4) arranged in an endoscope, wherein each said transmitter (4) comprises at least two mutually independent transmitting devices (6) that are integrated into a housing (5) of the device (2),
at least one receiver (8), wherein each said receiver (8) comprises two receiving components (10), and
the at least two transmitting devices (6) and the two receiving components being configured for communication over at least two wireless communication channels (11) that are independent of one another for each said transmitter and each said receiver, wherein the image transfer arrangement is configured to transmit data asynchronously via the at least two wireless communication channels, and wherein one of the wireless communication channels (11) is configured as bidirectional and another one of the wireless communication channels (11) is configured as unidirectional.

2. The endoscope system as claimed in claim 1, further comprising at least one of: the device being an image recording device (2) with at least one image sensor (3) that is connected or connectable to the transmitter (4), an image display device (7) that is connected or connectable to the receiver (8), or an additional image output device on the transmitter.

3. The endoscope system as claimed in claim 1, wherein at least one of: (a) one of the communication channels (11) is configured for transferring control at least one of commands or measurement data, or (b) at least one of the communication channels (11) is configured as an image channel.

4. The endoscope system as claimed in claim 1, wherein at least one of the transmitter (4) or the receiver (8) for each of the physical communication channels (11) in each case has at least one of an individual interface component (6, 10) or an individual address.

5. The endoscope system as claimed in claim 1, wherein the communication channels (11) are configured as at least one of a radio link or optical connection.

6. The endoscope system as claimed in claim 1, further comprising a preprocessor configured for delay-free image processing is disposed upstream of the transmitter (4).

7. The endoscope system as claimed in claim 1, wherein the transmitter (4) has at least one of a data or signal distributor, a multiplexer that feeds the at least two communication channels (11) with the at least one of data or signals, or an image divider that distributes image information items between the communication channels (11).

8. The endoscope system as claimed in claim 1, further comprising a marking device comprising a processor disposed upstream of the transmitter (4) and being configured to add a respective identification information item (23) to image information items communicated via the at least two communication channels (11), said respective identification information item (23) is adapted to allow for combining the transferred image information items at the receiver.

9. The endoscope system as claimed in claim 1, further comprising the device being an image recording device (2), and a memory (13) configured to store image information items that are present in the image recording device (2).

10. The endoscope system as claimed in claim 1, wherein each said communication channel (11) is feedable with data in a targeted manner.

11. An endoscope system, comprising:
an image recording device (2) having at least one image sensor (3) in an endoscope head of an endoscope, and
at least one transmitter (4) arranged in the endoscope and connected to the at least one image sensor and configured to asynchronously transmit image signals with at least two communication channels (11),
wherein each said transmitter (4) comprises at least two mutually independent transmitting devices (6),
at least one receiver (8), wherein each said receiver (8) comprises two receiving components (10), and
the at least two transmitting devices (6) and the two receiving components being configured for communication over the at least two wireless communication channels (11) that are independent of one another for each said transmitter and each said receiver to transmit the image signals asynchronously via the at least two wireless communication channels, wherein one of the wireless communication channels (11) is configured as bidirectional and another one of the wireless communication channels (11) is configured as unidirectional.

12. The endoscope system (14) as claimed in claim 11, further comprising at least one image display device (7), including:
    a receiver (8) with at least two communication channels (11) configured to receive the image signals, and
    a display screen (9) connected to the receiver (8).

13. A method for transferring image information items between a transmitter (4) and a receiver (8) in an endoscope system, the method comprising:
    providing an image transfer arrangement (1) including a device (2) with at least one transmitter (4) arranged in an endoscope, wherein each said transmitter (4) comprises at least two mutually independent transmitting devices (6) that are integrated into a housing (5) of the device (2), at least one receiver (8), wherein each said receiver (8) comprises two receiving components (10), and the at least two transmitting devices (6) and the two receiving components being configured for communication over at least two wireless communication channels (11) that are independent of one another;
    dividing an original total image into the image information items; and
    asynchronously transferring the image information items over the at least two independent communication channels (11) between each said transmitter and each said receiver, wherein one of the wireless communication channels (11) is configured as bidirectional and another one of the wireless communication channels (11) is configured as unidirectional.

14. The method as claimed in claim 13, further comprising:
    encoding an identification information item (23) in each of the image information items that are transferred over the communication channels (11), and
    forming a reconstruction of the original total image from the image information items using the encoding at a receiver end.

15. The method as claimed in claim 14, wherein the total image is divided between the at least two communication channels (11).

16. The method as claimed in claim 15, further comprising:
    if an image information item is missing in the reconstruction, omitting associated image information items that produce the reconstruction of the total image altogether, and presenting a previously reconstructed total instead.

17. The method as claimed in claim 13, further comprising:
    using one of the at least two communication channels (11) for transferring at least one of control commands or measurement data.

* * * * *